United States Patent
Mahó et al.

(10) Patent No.: US 9,676,814 B2
(45) Date of Patent: Jun. 13, 2017

(54) INDUSTRIAL PROCESS FOR THE SYNTHESIS OF ULIPRISTAL ACETATE AND ITS 4'-ACETYL ANALOGUE

(71) Applicant: RICHTER GEDEON NYRT., Budapest (HU)

(72) Inventors: Sándor Mahó, Budapest (HU); Csaba Sánta, Budapest (HU); János Csörgei, Budapest (HU); János Horváth, Budapest (HU); Antal Aranyi, Érd (HU); Zoltán Béni, Maglód (HU)

(73) Assignee: RICHTER GEDEON NYRT., Budapest (HU)

( * ) Notice: Subject to any disclaimer, the term of this patent is extended or adjusted under 35 U.S.C. 154(b) by 0 days.

(21) Appl. No.: 15/024,822

(22) PCT Filed: Oct. 1, 2014

(86) PCT No.: PCT/IB2014/064979
§ 371 (c)(1),
(2) Date: Mar. 24, 2016

(87) PCT Pub. No.: WO2015/049637
PCT Pub. Date: Apr. 9, 2015

(65) Prior Publication Data
US 2016/0311849 A1   Oct. 27, 2016

(30) Foreign Application Priority Data
Oct. 1, 2013   (HU) ..................................... 1300566

(51) Int. Cl.
| | | |
|---|---|---|
| C07J 5/00 | (2006.01) | |
| C07J 41/00 | (2006.01) | |
| C07J 7/00 | (2006.01) | |
| C07J 51/00 | (2006.01) | |
| C07J 21/00 | (2006.01) | |

(52) U.S. Cl.
CPC ......... *C07J 41/0083* (2013.01); *C07J 7/0045* (2013.01); *C07J 21/006* (2013.01); *C07J 51/00* (2013.01); *C07B 2200/07* (2013.01)

(58) Field of Classification Search
CPC .................................................. C07J 5/0053
USPC ..................................... 540/34, 36; 552/598
See application file for complete search history.

(56) References Cited

U.S. PATENT DOCUMENTS 4,954,490 A   9/1990 Cook et al.

FOREIGN PATENT DOCUMENTS

| CN | 102477060 A | 5/2012 |
|---|---|---|
| CN | 103601785 A | 2/2014 |
| WO | WO 96/30390 A2 | 10/1996 |
| WO | WO 99/45022 A1 | 9/1999 |
| WO | WO 01/74840 A2 | 10/2001 |
| WO | WO 2007/144674 A1 | 12/2007 |
| WO | WO 2009/001148 A2 | 12/2008 |
| WO | WO 2013/063859 A1 | 5/2013 |

OTHER PUBLICATIONS

International Search Report and Written Opinion for International Application No. PCT/IB2014/064979, European Patent Office, Netherlands, mailed on Jan. 13, 2015.
Cheng, X., et al., "A New and Efficient Method for the Synthesis of Ulipristal Acetate", *Steroids* 84:78-83, Elsevier Inc., United States (Mar. 2014).
Schwede, W., et al., "Synthesis and Biological Activity of 11, 19-Bridge Progestins", *Steroids* 63:166-177, Elsevier Science Inc., United States (1998).

*Primary Examiner* — Brenda Coleman
(74) *Attorney, Agent, or Firm* — Sterne, Kessler, Goldstein & Fox P.L.L.C.

(57) ABSTRACT

The present invention relates to a new process for the synthesis of compounds of formula (I) (wherein the meaning of R is dimethylamino or acetyl group) using the compound of formula (II) (wherein the meaning of R is dimethylamino or 2-methyl-1,3-dioxolan-2-yl group) as starting material, as well as to the intermediate of the process.

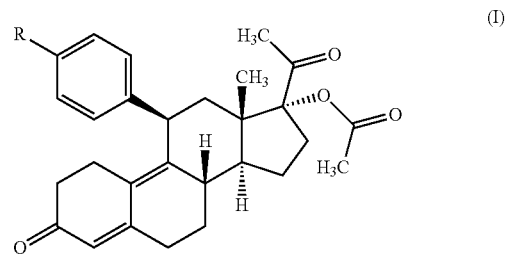

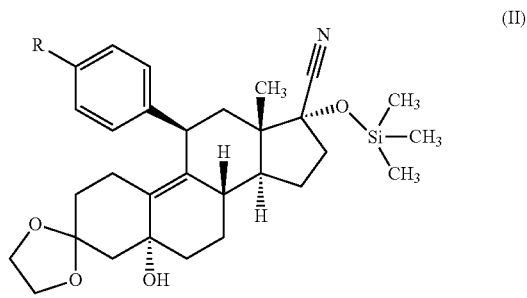

20 Claims, No Drawings

INDUSTRIAL PROCESS FOR THE SYNTHESIS OF ULIPRISTAL ACETATE AND ITS 4'-ACETYL ANALOGUE

The steroid compounds obtained according to the process of the present invention are progesterone derivatives.

Progesterone plays an important role in preparing the body for conception and maintaining pregnancy, besides it has effects on a number of tissues of the reproductive system. Selective progesterone receptor modulators can have both agonistic and antagonistic action via binding to progesterone receptor. They have different use within gynaecology. Antiprogestins, i.e. any substance that blocks the action of progesterone, can play a role in the pharmacological regulation of fertility and treatment of different diseases or pathological conditions, such as breast cancer and endometriosis. Antiprogestins were first used for contraception and emergency contraception, and besides of these for the treatment of other gynaecological diseases (for example uterine myoma).

The present invention relates to a new process for the synthesis of progesterone derivatives of formula (I) (wherein the meaning of R is dimethylamino or acetyl group)

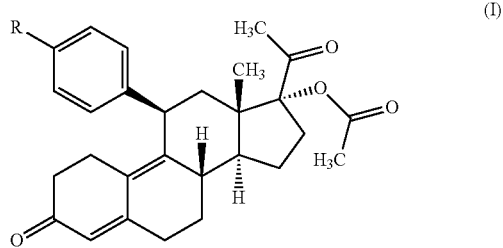

starting from the compound of formula (II) (wherein the meaning of R is dimethylamino or 2-methyl-1,3-dioxolan-2-yl group).

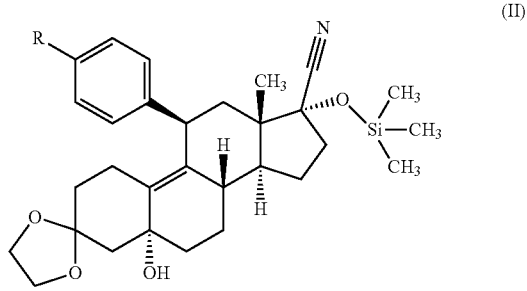

The compound of formula (I) (wherein the meaning of R is dimetilamino group) is a drug substance having sterane skeleton known as CDB-2914 ulipristal acetate. Ulipristal acetate is a selective progesterone receptor modulator (SPRM), it plays a role in governing those biological processes which are involved in the change of the progesterone level of the body.

Different processes have been elaborated for the synthesis of the compound of formula (I) (wherein the meaning of R is dimetilamino group), CDB-2914 (ulipristal acetate). The first synthesis was described in the U.S. Pat. No. 4,954,490, in which the starting material was 3-methoxy-19-norpregna-1,3,5(10),17(20)-tetraene. The 17(20) double bond was oxidized with osmium tetroxide to yield 17α,20α-diol, then the latter was transformed into 3-methoxy-19-norpregna-2,5 (10)-dien-17α,20α-diol by Birch reduction. Thereafter the 4,9-diene structure was formed with pyridinium tribromide to furnish 17α,20α-dihydroxy-19-norpregna-4,9-dien-3-one, which was oxidized with dimethyl sulfoxide in the presence of oxalyl chloride to yield 17α-hydroxy-19-norpregna-4,9-dien-3,20-dione. Then 3,3,20,20-bis(ethylenedioxy)-19-nor-pregna-5(10),9(11)-dien-17α-ol was formed with ketalization, which was epoxidated with m-chloroperbenzoic acid to furnish 5α,10α-epoxy-3,3,20,20-bis(ethylenedioxy)-19-norpregn-9(11)-en-17α-ol. Thereafter 3,3,20,20-bis(ethylenedioxy)-5α,17α-dihydroxy-11β-[4-(N,N-dimethylamino)-phenyl]-19-norpregn-9-en was obtained in a Grignard reaction with 4-(N,N-dimethylaminophenyl) magnesium bromide using CuCl as catalyst, which was acylated with a mixture of acetic anhydride and phosphoric acid to yield the compound of formula (I). The overall yield of this 10-step synthesis is 0.62%, therefore it is not suitable for an industrial scale synthesis of the drug substance.

The first industrial scale synthesis was described in the patent application No WO96/30390. The starting material of the synthesis is 17α-hydroxy-17β-cyanohydrine prepared from 3,3-ethylenedioxy-norandrosta-5(10),9(11)-dien-17-one, which was converted into 17β-cyano-3,3-ethylenedioxy-17α-(chloromethyl-dimethylsilyl)-estra-5(10),9(11)-diene with dimethyl (chloromethyl) chlorosilane in the presence of 4-(N,N-dimethylamino)pyridine. The obtained compound was transformed into a mixture of 17-hydroxy-19-norpregna-4,9-dien-3,20-dione and 5(10),9(11)-diene by intramolecular addition in the presence of lithium di-tert-butylbiphenyl followed by treatment with hydrochloric acid. This crude mixture was reacted with ethylene glycol and trimethyl orthoformate using p-toluenesulfonic acid as catalyst to yield 3,3,20,20-bis(ethylenedioxy)-17-hydroxy-19-norpregna-5(10),9(11)-diene. Then the 5(10) double bond was epoxidated with 30% hydrogen peroxide in the presence of hexafluoroacetone and disodium-phosphate. Thereafter 3,3,20,20-bis(ethylenedioxy)-5α,17-dihydroxy-11β-[4-(N,N-dimethylamino)-phenyl]-19-norpregn-9-en was obtained in a Grignard reaction with 4-(N,N-dimethylaminophenyl) magnesium bromide using CuCl as catalyst. The latter intermediate was hydrolyzed with acid and dehydrated to furnish 11β-[4-(N,N-dimethylamino)-phenyl]-17-hydroxy-19-norpregna-4,9-dien-3,20-dione, which was transformed into ulipristal acetate of formula (I) with trifluoroacetic anhydride in acetic acid in the presence of p-toluenesulfonic acid. The final product of formula (I) was obtained in eight steps starting from 3,3-ethylenedioxy-norandrosta-5(10),9(11)-dien-17-one.

The process published in Steroids 65 (2000), 395-400 is practically identical with the one described above.

The patent application No WO2009/001148 describes a modified process for the synthesis of the intermediates of ulipristal as compared to the previous ones. The starting material of the process was 3,3-[1,2-ethanediyl-bis-(oxy)]-estr-5(10),9(11)-dien-17-one, the 5(10) double bond of which was first epoxidated with hydrogen peroxide, then hydrogen cyanide, obtained from potassium cyanide and glacial acetic acid in situ, was added to the oxo group in position 17. The hydroxyl group in position 17 of the obtained cyanohydrine was silylated with trimethyl chlorosilane and the so formed product was reacted with 4-(N, N-dimethylaminophenyl)magnesium bromide in the presence of CuCl (Teutsch reaction). The hydroxyl group in position 5 of the so formed 11β-[4-(N,N-dimethylamino)-phenyl]-3,3-[1,2-ethanediyl-bis-(oxy)]-5-hydroxy-17α-

[trimethyl-silyl-(oxy)]-5α-estr-9-en-17β-carbonitrile was silylated with trimethyl chlorosilane to yield 11β-[4-(N,N-dimethylamino)-phenyl]-3,3-[1,2-ethanediyl-bis-(oxy)]-5,17α-bis[trimethyl-silyl-(oxy)]-5α-estr-9-en-17β-carbonitrile.

In the further part of the patent application No WO2009/001148 the intermediate obtained according to the method described above was used for the synthesis of telapriston (11β-[4-(N,N-dimethylamino)-phenyl]-17-hydroxy-21-methoxy-19-norpregna-4,9-dien-3,20-dione), which is an analogue of ulipristal.

The starting material of the process described in the patent application No CN102516345 was also 3,3-[1,2-ethanediyl-bis-(oxy)]-estr-5(10),9(11)-dien-17-one. This keton was reacted with sodium cyanide in methanol in the presence of glacial acetic acid, then the hydroxyl group of the obtained cyanohydrine was protected in the presence of p-toluenesulfonic acid. In the next step the cyanide group was methylated with methyllithium or methyl Grignard reagent in an ether-type solvent, then the 3-oxo-17β-acetyl derivative was obtained on treatment with strong acid. After protection of the oxo groups as ketals the double bond in position 5,10 was oxidized to epoxide, then the aromatic side-chain was introduced into position 11 with 4-(N,N-dimethylaminophenyl)magnesium bromide reagent. Both removal of the ketal-type protective groups and elimination of the hydroxyl group in position 5 were carried out in one step upon acidic treatment.

The key step of the synthesis route, the epoxidation reaction was carried out in relatively late phase of the process, in the fifth step. During the addition both 5α,10α- and 5β,10β derivatives were formed, which were used in the next Grignard reaction without separation. As the formation of the side-chain in position 17 was carried out in the third step the keto group of the side-chain had to be protected in order to avoid potential side-reactions, therefor the process had two more steps, the ketal formation and the deprotection, this way it was a seven-step reaction sequence. The reaction of the cyanohydrine steroid compound, protected as silyl ether, with methyllithium was an example in the patent application, this reaction was carried out at 0-10° C. According to our experiments several by-products were formed in the reaction at this relatively high temperature, therefor this method is not suitable for the alkylation of the cyanohydrine protected as silyl ether.

A further process for the synthesis of CDB-2914 was described in the patent application No WO2007/144674. The final product was obtained in eight steps starting from 3,3-ethylenedioxy-norandrosta-5(10),9(11)-dien-17-one. A further modification of the process is described in the Chinese patent application No CN102477060, wherein the order of the formation of side-chains in positions 11 and 17 was changed.

The acetyl derivative of formula (I) (wherein the meaning of R is acetyl) is a potential drug substance called REP-4510, the synthesis of which was first described in the patent application No WO01/74840. Similarly to the synthesis of the patent application No WO96/30390 the starting material was 3,3,20,20-bis(ethylenedioxy)-17-hydroxy-19-norpregna-5(10),9(11)-diene, which was epoxidated, then reacted with the Grignard reagent formed from the ketal of 4-bromo-acetophenon (Teutsch reaction) to furnish 3,20-bis-ethyl enedioxy-5,17-dihydroxy-11β-[4-(2-methyl-1,3-dioxolan-2-yl)phenyl]-19-nor-5α-pregn-9-ene, from which after removal of the protective groups in a sulfuric acid containing medium, and reaction with the mixed anhydride formed from acetic anhydride and trifluoroacetic anhydride the final product, the 17 acetoxy derivative was obtained.

Taking into consideration the above facts, there continues to be a need for elaboration of an industrial process for the synthesis of the final product of formula (I), which is more economical and more environment friendly than the known ones.

Surprisingly it was found that the following process fulfils the above requirements:

a) the compound of formula (II) (wherein the meaning of R is dimethylamino or 2-methyl-1,3-dioxolan-2-yl group)

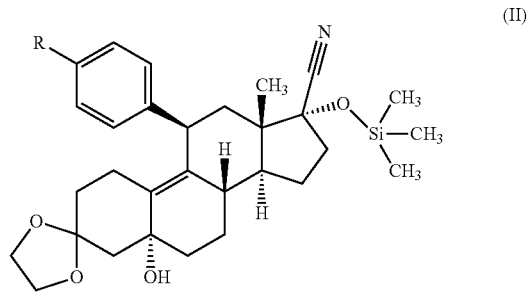

(II)

is reacted with 2-15 mol equivalent methyllithium in the presence of tetraalkyl ethylenediamine in ether or formaldehyde acetal type solvent or in the mixture thereof at a temperature between −78-(−20)° C., then the protected imine obtained as intermediate is reacted with a mineral or strong organic acid at a temperature between 0° C. and the boiling point of the used organic solvent. The excess of methyllithium is preferably 5-15 mol equivalent, the used tetraalkyl ethylenediamine is preferably tetramethyl ethylenediamine. The ratio of tetraalkyl ethylenediamine/methyllithium is preferably 0.5:1-5:1. The solvents preferably used are diethyl ether, tetrahydrofuran, methyltetrahydrofuran, methyl tert-butyl ether, diisopropyl ether, diethoxymethane, dimethoxymethane, more preferably tetrahydrofuran, dimethoxy- and diethoxymethane. The temperature of the reaction is preferably between −50-(−30)° C. In the reaction of the imine obtained as intermediate the applied mineral or strong organic acid can preferably be hydrochloric acid, sulfuric acid, potassium hydrogensulfate, sodium hydrogensulfate, p-toluenesulfonic acid or perchloric acid, more preferably sulfuric acid. The transformation of the imine is carried out in a solvent miscible with water, for example alcohol or ether miscible with water, preferably methanol, ethanol or tetrahydrofuran. The temperature of the reaction is preferably between 20-50° C., then the hydroxyl group in position 17 of the obtained compound of formula (IV) (wherein the meaning of R is as described for formula (I))

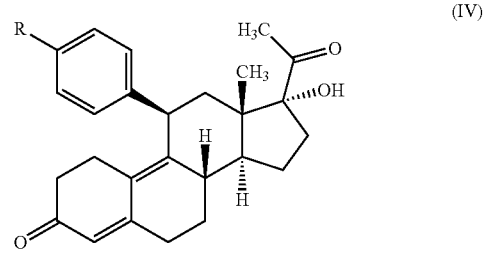

(IV)

is acetylated with acetic anhydride in a halogenated solvent, preferably dichloromethane, in the presence of 70% perchloric acid at a temperature between −78-0° C., then the obtained compound of formula (I) (wherein the meaning of R is dimethylamino or acetyl group) in given case is recrystallized from methanol or ethanol; or b) the hydroxyl group in position 5 of the compound of formula (II) (wherein the meaning of R is dimethylamino or 2-methyl-1,3-dioxolan-2-yl group)

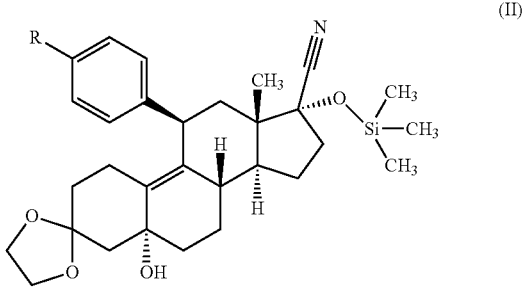

is silylated with chlorotrimethyl silane in the presence of imidazole in a halogenated solvent, tetrahydrofuran or toluene, preferably in dichloromethane at room temperature; then the obtained compound of formula (III) (wherein the meaning of R is as described for formula (II))

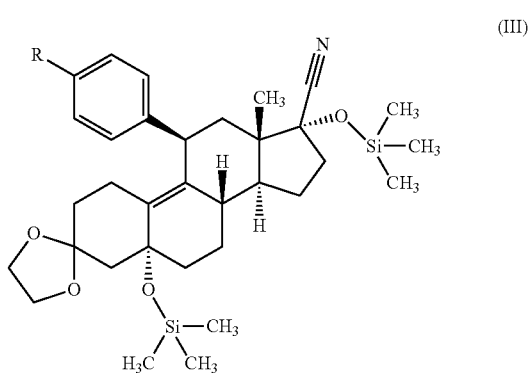

is reacted with 2-15 mol equivalent of methyllithium in the presence of tetraalkyl ethylenediamine in an ether or formaldehyde acetal type solvent or in the mixture thereof at a temperature between −78-(−20)° C., then the protected imine obtained as intermediate is reacted with a mineral or strong organic acid at a temperature between 0° C. and the boiling point of the used organic solvent. The excess of methyllithium is preferably 5-15 mol equivalent, the used tetraalkyl ethylenediamine is preferably tetramethyl ethylenediamine. The ratio of tetraalkyl ethylenediamine/methyllithium is preferably 0.5:1-5:1. The solvents preferably used are diethyl ether, tetrahydrofuran, methyltetrahydrofuran, methyl tert-butyl ether, diisopropyl ether, diethoxymethane, dimethoxymethane, more preferably tetrahydrofuran, dimethoxy- and diethoxymethane. The temperature of the reaction is preferably between −50-(−30)° C. In the reaction of the imine obtained as intermediate the applied mineral or strong organic acid can preferably be hydrochloric acid, sulfuric acid, potassium hydrogensulfate, sodium hydrogensulfate, p-toluenesulfonic acid or perchloric acid, more preferably sulfuric acid. The transformation of the imine is carried out in a solvent miscible with water, for example alcohol or ether miscible with water, preferably methanol, ethanol or tetrahydrofuran. The temperature of the reaction is preferably between 20-50° C., then the hydroxyl group in position 17 of the obtained compound of formula (IV) (wherein the meaning of R is as described for formula (I))

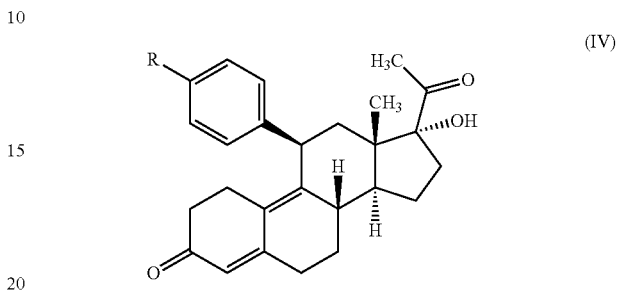

is acetylated with acetic anhydride in a halogenated solvent, preferably dichloromethane, in the presence of 70% perchloric acid at a temperature between −78-0° C., then the obtained compound of formula (I) (wherein the meaning of R is dimethylamino or acetyl group) in given case is recrystallized from methanol or ethanol.

The starting material of formula (II) is obtained according to the process described in the patent application No WO2009/001148 starting from 3,3-[1,2-ethanediyl-bis-(oxy)]-estr-5(10),9(11)-dien-17-one.

Preferably first the diethoxymethane solution of methyllithium is added to the solution of the carbonitrile of formula (II) below −45° C., then the tetramethyl ethylenediamine is added. Then the reaction mixture is stirred at a temperature between −45-(−40)° C. for 3 hours. The reaction is quenched with the addition of water, while the temperature of the reaction mixture is allowed to rise to +20° C. After stirring the phases were separated, the organic phase is concentrated at reduced pressure, and the residue is stirred with methanol and 1N sulfuric acid at 40° C. After basification the precipitated material is filtered off and recrystallized from a mixture of ethanol and water.

The hydroxyl group in position 17 of the obtained diketon of formula (IV) is acetylated with acetic anhydride in dichloromethane in the presence of 70% perchloric acid at a temperature between −78-0° C., then the obtained final product of formula (I) is recrystallized from methanol.

In a further embodiment of the present invention the hydroxyl group in position 5 of the carbonitrile of formula (II) is preferably silylated with chloromethyl silane in the presence of imidazole in dichloromethane at room temperature, then the diethoxymethane solution of methyllithium is added to the solution of the obtained carbonitrile of formula (III) below −40° C., then the tetramethyl ethylenediamine is added. Then the reaction mixture is stirred at a temperature between −40-(−35)° C. for 3 hours. The reaction is quenched with the addition of water, while the temperature of the reaction mixture is allowed to rise to +20° C. After stirring the phases were separated, the organic phase is concentrated at reduced pressure, and the residue is stirred with methanol and 1N sulfuric acid at 40° C. After basification the precipitated material is filtered off and recrystallized from a mixture of ethanol and water.

The hydroxyl group in position 17 of the obtained diketon of formula (IV) is acetylated with acetic anhydride in dichloromethane in the presence of 70% perchloric acid at a temperature between −78-0° C., then the obtained final product of formula (I) is recrystallized from methanol.

Advantages of the process of the invention:

a) the use of tetraalkyl ethylenediamine is beneficial as the reaction can be carried out at lower temperature and side reactions can be eliminated;

b) the formation of the keto group of the side-chain in position 17 is carried out in the last step of the reaction sequence, therefor the protection and deprotection steps are unnecessary;

c) according to the process of this invention the final product of formula (I) is obtained in less steps, four or five steps, as compared to the previous processes starting from 3,3-[1,2-ethanediyl-bis-(oxy)]-estr-5(10),9(11)-dien-17-one.

EXAMPLES

Example 1

Synthesis of 11β-[4-(N,N-dimethylamino)-phenyl]-17-hydroxy-19-norpregna-4,9-dien-3,20-dione 8.0 g (14.5 mM) of 11β-[4-(N,N-dimethylamino)-phenyl]-3,3-ethylenedioxy-5α-hydroxy-17α-[(trimethylsilyl)oxy]-5α-estr-9-en-17β-carbonitrile was dissolved in 130 ml of tetrahydrofuran and the solution was cooled to −50° C. First 60 ml (180 mM) of methyllithium 3.0 M solution in diethoxymethane, then 27 ml (180 mM) of tetramethyl ethylenediamine were added dropwise at such a rate to keep the reaction temperature below −45° C. The reaction mixture was stirred at a temperature between −45-(−40)° C. for 3 hours, then 70 ml of water was added dropwise very carefully to the reaction mixture while the temperature was allowed to rise to +20° C. After stirring for 5 min the phases were separated, the organic phase was washed with 20 ml of water, then it was concentrated at reduced pressure. 80 ml of methanol and 110 ml of 1N sulfuric acid solution were added to the residue and the homogeneous solution was stirred at 40° C. for 3 hours. This acidic solution was poured into a solution of 5.8 g of sodium carbonate in 720 ml of water, then the precipitated material was filtered off and washed with water until neutral pH. The obtained 5.2 g of crude product was recrystallized from a mixture of ethanol and water to yield 4.4 g (70%) of the title compound.

Melting point: 188-190° C.

$^1$H NMR (500 MHz, CDCl$_3$) δ: 6.95-7.01 (m, 2H), 6.58-6.70 (m, 2H), 5.76 (s, 1H), 4.36 (m, 1H), 3.12 (s, 1H), 2.91 (s, 6H), 2.71-2.78 (m, 1H), 2.64 (m, 1H), 2.59 (dd, J=8.3, 4.4 Hz, 2H), 2.47-2.54 (m, 1H), 2.29-2.46 (m, 4H), 2.26 (s, 3H), 1.97-2.07 (m, 3H), 1.84-1.95 (m, 1H), 1.69-1.80 (m, 1H), 1.60-1.69 (m, 1H), 1.47-1.58 (m, 1H), 1.42 (qd, J=12.0, 6.1 Hz, 1H), 0.46 (s, 3H) ppm $^{13}$C NMR (125 MHz, CDCl$_3$) δ: 211.7, 199.7, 156.8, 148.5, 146.1, 131.9, 129.1, 127.4, 122.7, 112.7, 89.6, 49.9, 48.7, 40.6, 39.3, 38.1, 36.9, 35.9, 33.2, 31.0, 28.0, 27.9, 25.8, 24.3, 16.9 ppm Example 2

Synthesis of 11β-[4-(N,N-dimethylamino)-phenyl]-17-hydroxy-19-norpregna-4,9-dien-3,20-dione 25.0 g (40.1 mM) of 11β-[4-(N,N-dimethylamino)-phenyl]-3,3-ethylenedioxy-5,17α-bis[(trimethylsilyl)oxy]-5α-estr-9-en-17β-carbonitrile was dissolved in 500 ml of dimethoxymethane and the solution was cooled to −50° C. First 66.7 ml (200 mM) of methyllithium 3.0 M solution in diethoxymethane, then 30 ml (200 mM) of tetramethyl ethylenediamine were added dropwise at such a rate to keep the reaction temperature below −40° C. The reaction mixture was stirred at a temperature between −45-(−35)° C. for 3 hours, then 210 ml of water was added dropwise very carefully to the reaction mixture while the temperature was allowed to rise to +20° C. After stirring for 5 min the phases were separated, the organic phase was washed with 50 ml of water, then it was concentrated at reduced pressure. 220 ml of methanol and 300 ml of 1N sulfuric acid solution were added to the residue and the homogeneous solution was stirred at 40° C. for 3 hours. This acidic solution was poured into a solution of 16 g of sodium carbonate in 2 l of water, then the precipitated material was filtered off and washed with water until neutral pH. The obtained 14.7 g of crude product was recrystallized from a mixture of ethanol and water to yield 12.3 g (70.7%) of the title compound.

Melting point: 188-190° C.

$^1$H NMR (500 MHz, CDCl$_3$) δ: 6.95-7.01 (m, 2H), 6.58-6.70 (m, 2H), 5.76 (s, 1H), 4.36 (m, 1H), 3.12 (s, 1H), 2.91 (s, 6H), 2.71-2.78 (m, 1H), 2.64 (m, 1H), 2.59 (dd, J=8.3, 4.4 Hz, 2H), 2.47-2.54 (m, 1H), 2.29-2.46 (m, 4H), 2.26 (s, 3H), 1.97-2.07 (m, 3H), 1.84-1.95 (m, 1H), 1.69-1.80 (m, 1H), 1.60-1.69 (m, 1H), 1.47-1.58 (m, 1H), 1.42 (qd, J=12.0, 6.1 Hz, 1H), 0.46 (s, 3H) ppm $^{13}$C NMR (125 MHz, CDCl$_3$) δ: 211.7, 199.7, 156.8, 148.5, 146.1, 131.9, 129.1, 127.4, 122.7, 112.7, 89.6, 49.9, 48.7, 40.6, 39.3, 38.1, 36.9, 35.9, 33.2, 31.0, 28.0, 27.9, 25.8, 24.3, 16.9 ppm Example 3

Synthesis of 3,3-ethylenedioxy-11β-[4-(2-methyl-1,3-dioxolan-2-yl)-phenyl]-5,17α-bis[(trimethylsilyl)oxy]-5α-estr-9-en-17β-carbonitrile 25.0 g (41.68 mM) of 3,3-ethylenedioxy-11β-[4-(2-methyl-1,3-dioxolan-2-yl)-phenyl]-5-hydroxy-17α-[(trimethylsilyl)oxy]-5α-estr-9-en-17β-carbonitrile (Example 25 of WO2001/74840) was dissolved in 125 ml of dichloromethane, 5 g of imidazole and then 8.4 ml of chlorotrimethylsilane were added dropwise to the solution at 20° C. The reaction mixture was stirred at 20-25° C. for 1 hour, then it was diluted with 70 ml of dichloromethane and 70 ml of water. After vigorous stirring for 10 min the phases were separated, the organic phase was washed with 2×50 ml of water, dried over anhydrous sodium sulfate and concentrated. The residue was recrystallized from methanol to yield 22.2 g (80.0%) of the title compound.

Melting point: 134-135° C.

$^1$H NMR (800 MHz, CDCl$_3$) δ: 7.34 (m, 2H), 7.16 (m, 2H), 4.33 (m, 1H), 3.99-4.05 (m, 2H), 3.96 (m, 1H), 3.88-3.94 (m, 1H), 3.83-3.88 (m, 1H), 3.77-3.83 (m, 2H), 3.73-3.77 (m, 1H), 2.37-2.46 (m, 1H), 2.24-2.35 (m, 3H), 2.21 (dd, J=14.4, 2.6 Hz, 1H), 2.12-2.18 (m, 1H), 2.04 (m, 1H), 2.08 (dd J=14.4, 0.9 Hz, 1H) 1.97 (ddd, J=14.8, 9.1, 5.5 Hz, 1H), 1.75-1.88 (m, 2H), 1.65-1.73 (m, 4H), 1.64 (s, 3H), 1.47-1.57 (m, 1H), 1.34 (m, 1H), 1.20 (td, J=12.8, 4.0 Hz, 1H), 0.48 (s, 3H), 0.26 (s, 9H), 0.18 (s, 9H) ppm $^{13}$C NMR (200 MHz, CDCl$_3$) δ: 145.9, 140.3, 136.2, 132.6, 126.9, 125.1, 120.9, 108.8, 108.4, 78.8, 73.5, 64.5, 64.5, 64.4, 63.4, 50.1, 49.0, 47.2, 38.9, 38.6, 38.5, 35.6, 34.9, 27.4, 24.6, 24.5, 23.5, 17.0, 2.6, 1.1 ppm

Example 4

Synthesis of 11β-(4-acetylphenyl)-17-hydroxy-19-norpregna-4,9-dien-3,20-dion 10.0 g (15.0 mM) of 3,3-ethylenedioxy-11β-[4-(2-methyl-1,3-dioxolan-2-yl)-phenyl]-5,17α-bis[(trimethylsilyl)oxy]-5α-estr-9-en-17β-carbonitrile was dissolved in 150 ml of dimethoxymethane and the solution was cooled to −50° C. First 50 ml (150 mM) of methyllithium 3.0 M solution in diethoxymethane, then 22.5 ml (150 mM) of tetramethyl ethylenediamine were added dropwise at such a rate to keep the reaction temperature below −45° C. The reaction mixture was stirred at a temperature between −45-(−40)° C. for 5 hours, then 70 ml of water was added dropwise very carefully to the reaction mixture while the temperature was allowed to rise to +20° C. After stirring for 5 min the phases were separated, the organic phase was washed with 20 ml of water, then it was concentrated at reduced pressure. 150 ml of tetrahydrofuran and 50 ml of 10% hydrochloric acid solution were added to the residue and the mixture was stirred for 1 hour, then 100 ml of dichloromethane was added and the mixture was cooled to 10° C. It was neutralized with 14 ml of 25% ammonia solution and after 5 min stirring the phases were separated. The organic phase was washed with water until neutral pH, dried over anhydrous sodium sulfate and concentrated. The residue was recrystallized from a acetone to yield 5.13 g (79.0%) of the title compound.

$^1$H NMR (500 MHz, CDCl$_3$) δ: 7.80-7.93 (m, 2H), 7.20-7.30 (m, 2H), 5.79 (s, 1H), 4.48 (m, 1H), 3.22 (br. s., 1H), 2.72 (dt, J=15.2, 5.5 Hz, 1H), 2.59-2.67 (m, 3H), 2.57 (s, 3H), 2.52 (dd, J=13.3, 7.9 Hz, 2H), 2.39-2.47 (m, 1H), 2.30-2.38 (m, 1H), 2.20-2.30 (m, 4H), 1.99-2.14 (m, 4H), 1.88-1.98 (m, 1H), 1.76-1.88 (m, 1H), 1.66 (ddd, J=15.1, 9.4, 6.1 Hz, 1H), 1.55 (dq, J=12.8, 9.0 Hz, 1H), 1.34-1.49 (m, 1H), 0.40 (s, 3H) ppm $^{13}$C NMR (125 MHz, CDCl$_3$) δ: 211.5, 199.2, 197.5, 156.1, 150.5, 144.1, 135.0, 129.9, 128.7, 127.1, 123.3, 89.4, 49.6, 48.6, 40.4, 38.2, 36.7, 36.2, 33.2, 31.0, 28.0, 27.8, 26.5, 25.8, 24.2, 16.8 ppm

Example 5

Synthesis of 17-acetoxy-11β-[(4-(N,N-dimethylamino)-phenyl]-19-norpregna-4,9-dien-3,20-dione 12.0 g (27.7 mM) of 11β-[4-(N,N-dimethylamino)-phenyl]-17-hydroxy-19-norpregna-4,9-dien-3,20-dione was dissolved in 72 ml of dichloromethane and 38 ml (402 mM) of acetic anhydride was added. The reaction mixture was cooled to −25 (−20)° C. and 5.2 ml (60.6 mM) of 70% perchloric acid was added dropwise over a period of 15-20 min. The reaction mixture was stirred at a temperature between 25 (−20)° C. for 30 min, then it was poured into a cooled (0-(−5)° C.) mixture of 64 ml of 25% aqueous ammonia and 100 ml of water. The obtained mixture was diluted with 70 ml of dichloromethane and stirred at 20-25° C. for 30 min. The phases were separated, the organic phase was washed with 2×50 ml of water, dried over anhydrous sodium sulfate, filtered and concentrated in vacuum. The residue was recrystallized form methanol to yield 11.2 g (85%) of title compound.

Melting point: 184-186° C.

$^1$H NMR (CDCl$_3$, 500 MHz) δ: 6.95-7.01 (m, 2H), 6.61-6.69 (m, 2H), 5.78 (s, 1H), 4.39 (d, J=7.3 Hz, 1H), 2.91 (s, 6H), 2.84-2.90 (m, 1H), 2.78 (ddd, J=15.0, 5.6, 5.3 Hz, 1H), 2.56-2.63 (m, 3H), 2.48-2.56 (m, 1H), 2.42-2.48 (m, 1H), 2.30-2.41 (m, 2H), 2.20 (d, J=13.2 Hz, 1H), 2.13 (s, 3H), 2.10 (s, 3H), 2.05 (dq, J=12.7, 4.4 Hz, 1H), 1.92-2.02 (m, 1H), 1.74-1.88 (m, 2H), 1.46-1.57 (m, 1H), 1.32-1.42 (m, 1H), 0.36 (s, 3H) ppm $^{13}$C NMR (CDCl$_3$, 125 MHz) δ: 203.8, 199.5, 170.6, 156.5, 145.6, 129.3, 127.3, 122.9, 112.8, 96.2, 50.9, 47.0, 40.6, 39.3, 38.3, 36.8, 36.7, 31.0, 30.2, 27.8, 26.8, 25.8, 24.2, 21.2, 15.6 ppm

Example 6

Synthesis of 17-acetoxy-11β-(4-acetyl-phenyl)-19-norpregna-4,9-dien-3,20-dione 5.0 g (11.6 mM) of 11β-(4-acetylphenyl)-17-hydroxy-19-norpregna-4,9-dien-3,20-dion was dissolved in 50 ml of dichloromethane and 17 ml (180 mM) of acetic anhydride was added. The reaction mixture was cooled to −25-(−20)° C. and 2.3 ml (38.2 mM) of 70% perchloric acid was added dropwise over a period of 15-20 min. The reaction mixture was stirred at a temperature between −25-(−20)° C. for 30 min, then it was poured into a cooled (0-(−5)° C.) mixture of 30 ml of 25% aqueous ammonia and 50 ml of water. The obtained mixture was diluted with 50 ml of dichloromethane and stirred at 20-25° C. for 30 min. The phases were separated, the organic phase was washed with 2×50 ml of water, dried over anhydrous sodium sulfate, filtered and concentrated in vacuum. The residue was recrystallized form methanol to yield 4.56 g (83%) of title compound.

Melting point: 249-252° C.

$^1$H NMR (CDCl$_3$, 500 MHz) δ: 7.84-7.90 (m, 2H), 7.24-7.28 (m, 2H), 5.81 (s, 1H), 4.50 (d, J=7.6 Hz, 1H), 2.81-2.93 (m, 1H), 2.67-2.79 (m, 2H), 2.63 (dd, J=8.1, 3.4 Hz, 2H), 2.57 (s, 3H), 2.41-2.55 (m, 2H), 2.32-2.41 (m, 1H), 2.20-2.32 (m, 2H), 2.14 (s, 3H), 2.08-2.12 (m, 1H), 2.05-2.09 (m, 1H), 1.99 (td, J=12.3, 6.6 Hz, 1H), 1.76-1.91 (m, 2H), 1.47-1.62 (m, 1H), 1.29-1.45 (m, 1H), 0.30 (s, 3H) ppm $^{13}$C NMR (CDCl$_3$, 125 Mhz) δ: 203.6, 199.0, 197.4, 170.4, 155.8, 150.1, 143.4, 135.1, 130.1, 128.8, 127.0, 123.5, 95.7, 50.6, 47.0, 40.4, 38.4, 37.0, 36.7, 31.0, 30.3, 27.8, 27.0, 26.5, 25.8, 24.1, 21.2, 15.6 ppm

The invention claimed is:

1. A process for the synthesis of a compound of formula (I)

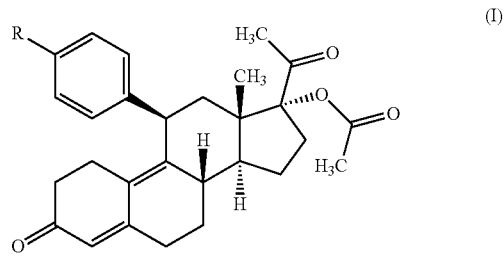

wherein R in formula (I) is a dimethylamino or an acetyl group, the process comprises
a) (1) reacting the compound of formula (II), wherein R in formula (II) is a dimethylamino or a 2-methyl-1,3-dioxolan-2-yl group,

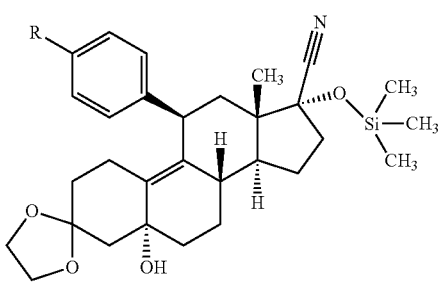

(II)

with 2-15 mol equivalent methyllithium in the presence of tetraalkyl ethylenediamine in an ether or a formaldehyde acetal type solvent, or in a mixture thereof, at a temperature of between (−78° C.) and (−20° C.), (2) reacting the protected imine intermediate obtained from (1) with a mineral or a strong organic acid at a temperature between 0° C. and the boiling point of the organic solvent, (3) acetylating the hydroxyl group in position 17 of the compound of formula (IV) obtained from (2), wherein R in formula (IV) is as described for formula (I),

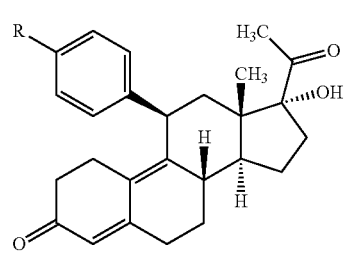

(IV)

with acetic anhydride in a halogenated solvent, in the presence of 70% perchloric acid, and at a temperature of between (−78° C.) and 0° C., and (4) recrystallizing the compound of formula (I) obtained from (3) from methanol or ethanol;

or b) (1) silylating the hydroxyl group in position 5 of the compound of formula (II), wherein R in formula (II) is a dimethylamino or a 2-methyl-1,3-dioxolan-2-yl group,

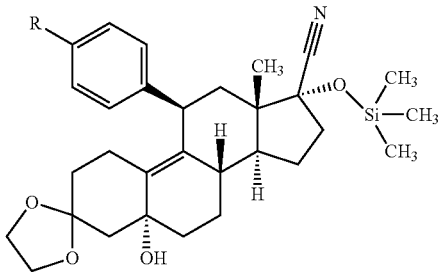

(II)

with chloromethyl silane in the presence of imidazole in a halogenated solvent, tetrahydrofuran or toluene, at room temperature;

(2) reacting the compound of formula (III) obtained from (1), wherein R in formula (III) is as described for formula (II),

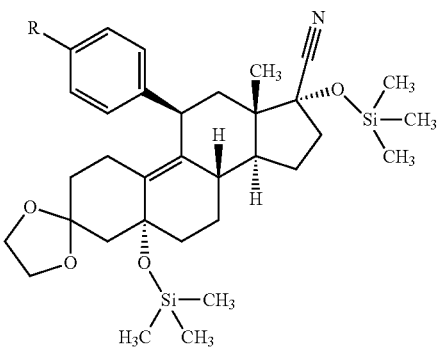

with 2-15 mol equivalent of methyllithium in the presence of tetraalkyl ethylenediamine in an ether or a formaldehyde acetal type solvent, or in a mixture thereof, at a temperature of between (−78° C.) and (−20° C.), (3) reacting the protected imine intermediate obtained from (2) with a mineral or a strong organic acid at a temperature between 0° C. and the boiling point of the organic solvent, (4) acetylating the hydroxyl group in position 17 of the compound of formula (IV) obtained from (3), wherein R in formula (IV) is as described for formula (I),

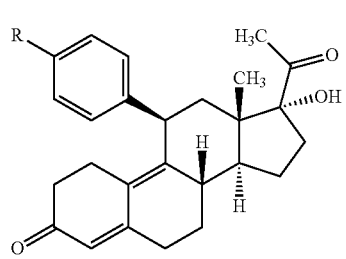

(IV)

with acetic anhydride in a halogenated solvent, in the presence of 70% perchloric acid, at a temperature of between (−78° C.) and 0° C., and (5) recrystallizing the compound of formula (I) obtained from (4), wherein R is a dimethylamino or an acetyl group, from methanol or ethanol.

2. The process of claim 1, wherein the process comprises using an excess of 5-15 mol equivalent of methyllithium in step 1 of process a) or step 2 of process b).

3. The process of claim 1, wherein the tetraalkyl ethylenediamine in step 1 of process a) or step 2 of process b) is tetramethyl ethylenediamine.

4. The process of claim 1, wherein the ratio of tetraalkyl ethylenediamine/methyllithium is 0.5:1-5:1 in step 1 of process a) or step 2 of process b).

5. The process of claim 1, wherein the solvent in step 1 of process a) or step 2 of process b) is diethyl ether, tetrahydrofuran, methyltetrahydrofuran, methyl tert-butyl ether, diisopropyl ether, diethoxymethane, or dimethoxymethane.

6. The process of claim 1, wherein the temperature of the reaction in step 1 of process a) or step 2 of process b) is between (−50° C.) and (−30° C.).

7. The process of claim 1, wherein the mineral or strong organic acid is hydrochloric acid, sulfuric acid, potassium hydrogensulfate, sodium hydrogensulfate, p-toluenesulfonic acid, or perchloric acid.

8. The process of claim 1, wherein the solvent in step 1 of process a) or step 2 of process b) is a solvent miscible with water.

9. The process of claim 1, wherein the temperature in step 2 of process a) or step 3 of process b) is between 20-50° C.

10. The compound of formula (III), wherein R is a 2-methyl-1,3-dioxolan-2-yl group.

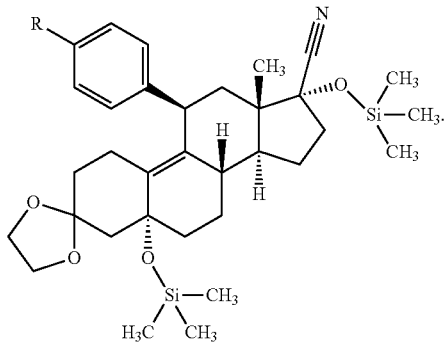

11. The process of claim 5, wherein the solvent in step 1 of process a) or step 2 of process b) is tetrahydrofuran, dimethoxymethane, or diethoxymethane.

12. The process of claim 7, wherein the mineral or strong organic acid is sulfuric acid.

13. The process of claim 8, wherein the solvent miscible with water is methanol, ethanol, or tetrahydrofuran.

14. The process of claim 13, wherein the solvent miscible with water is methanol.

15. The process of claim 9, wherein the temperature in step 2 of process a) or step 3 of process b) is from 20 to 25° C.

16. The process of 1, wherein the halogenated solvent is dichloromethane.

17. The process of claim 1, wherein the temperature of step 1 of process a) or step 2 of process b) is between (−45° C.) and (−40° C.).

18. The process of claim 1, wherein R of the compound of formula (I) is a dimethylamino group.

19. The process of claim 1, wherein R of the compound of formula (I) is an acetyl group.

20. The process of claim 9, wherein the temperature in step 2 of process a) or step 3 of process b) is from 25 to 50° C.

* * * * *

UNITED STATES PATENT AND TRADEMARK OFFICE
CERTIFICATE OF CORRECTION

PATENT NO.        : 9,676,814 B2  
APPLICATION NO.   : 15/024822  
DATED             : June 13, 2017  
INVENTOR(S)       : Mahó et al.

Page 1 of 2

It is certified that error appears in the above-identified patent and that said Letters Patent is hereby corrected as shown below:

In Column 12, Line 5, Claim 1, the structure of formula (III) should appear as follows:

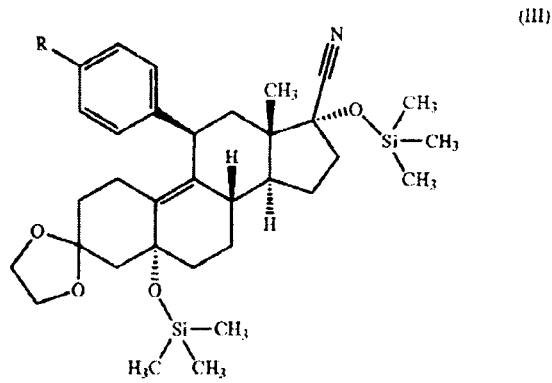

In Column 13, Line 10, Claim 10, delete "The compound of formula (III), wherein R is a 2-methyl-1,3-dioxolan-2-yl group.

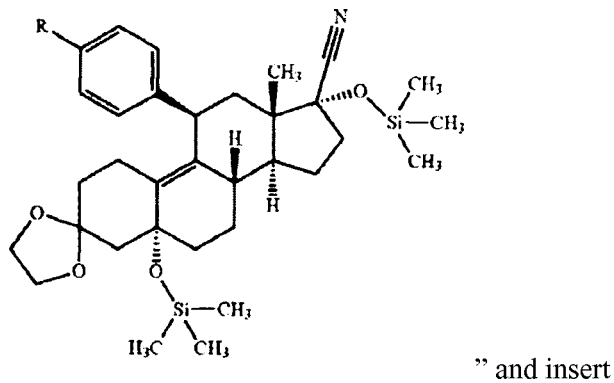

" and insert

Signed and Sealed this  
Twenty-first Day of November, 2017

Joseph Matal  
*Performing the Functions and Duties of the  
Under Secretary of Commerce for Intellectual Property and  
Director of the United States Patent and Trademark Office*

--The compound of formula (III),
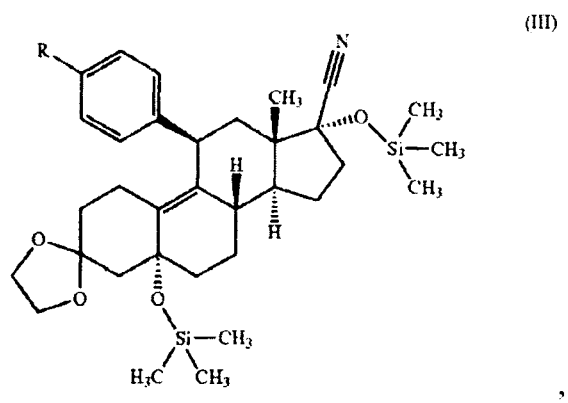
wherein R is a 2-methyl-1,3-dioxolan-2-yl group.--
In Column 14, Line 14, Claim 16, delete "The process of 1," and insert --The process of claim 1,--